US005601435A

United States Patent [19]

Quy

[11] Patent Number: 5,601,435
[45] Date of Patent: Feb. 11, 1997

[54] METHOD AND APPARATUS FOR INTERACTIVELY MONITORING A PHYSIOLOGICAL CONDITION AND FOR INTERACTIVELY PROVIDING HEALTH RELATED INFORMATION

[75] Inventor: Roger J. Quy, Belvedere, Calif.

[73] Assignee: Intercare, Irvine, Calif.

[21] Appl. No.: 334,643

[22] Filed: Nov. 4, 1994

[51] Int. Cl.⁶ ...................................................... G09B 5/00
[52] U.S. Cl. ..................... 434/307 R; 434/262; 434/365; 395/501; 364/413.02
[58] Field of Search ................................... 434/247, 118, 434/262, 265, 307 R, 308, 318, 362, 365; 364/413.01–413.04, 578; 395/154, 152; 128/630

[56] References Cited

U.S. PATENT DOCUMENTS

| | | |
|---|---|---|
| 4,130,881 | 12/1978 | Haessler et al. . |
| 4,347,851 | 9/1982 | Jundanian . |
| 4,360,345 | 11/1982 | Hon ......................................... 434/262 |
| 4,576,578 | 3/1986 | Parker et al. ....................... 434/307 R |
| 4,729,381 | 3/1988 | Harada et al. . |
| 4,779,199 | 10/1988 | Yoneda et al. . |
| 4,796,639 | 1/1989 | Snow et al. . |
| 4,803,625 | 2/1989 | Fu et al. . |
| 4,907,973 | 3/1990 | Hon ...................................... 434/307 R |
| 4,933,873 | 6/1990 | Kaufman et al. . |
| 5,024,225 | 6/1991 | Fang . |
| 5,025,374 | 6/1991 | Roizen et al. . |
| 5,056,059 | 10/1991 | Tivig et al. . |
| 5,120,230 | 6/1992 | Clark et al. ......................... 434/307 R |
| 5,222,020 | 6/1993 | Takeda . |
| 5,307,263 | 4/1994 | Brown . |
| 5,454,722 | 10/1995 | Holland et al. ....................... 434/308 X |

OTHER PUBLICATIONS

"Who Will Dominate The Desktop In the '90s?" by Jack Shandle, Electronics, Feb. 1990, pp. 48–50.

*Primary Examiner*—Joe Cheng
*Attorney, Agent, or Firm*—Haverstock & Associates

[57] ABSTRACT

An electronic health monitoring system. A multimedia processor is a modified CD-ROM multimedia interactive television video game console which comprises a microprocessor, hardware, and software. One or more physiological data monitors are coupled to provide a signal representative of a user's physiological parameter to the multimedia processor through an isolated interface circuit. A hand-held program controller with directional buttons is operated by the user to control the various functions of the multimedia processor. A television is coupled to the multimedia processor to provide sound and a video display based upon output signals from the multimedia processor.

Interchangeable compact disks (CD-ROM) comprise additional software. The software contained in the interchangeable compact disks enables the system to execute a variety of health related functions, to display high quality moving or still video images and to produce high quality sound accompaniment. For example, the system may monitor a user's electrocardiographic signals and display an ECG waveform and various other parameters, such as heart rate, on the television screen. The system may also interactively provide more detailed or educational information to the user based upon the user's operation of the hand-held program controller and also based upon predetermined software routines and data stored within the system.

30 Claims, 1 Drawing Sheet

METHOD AND APPARATUS FOR INTERACTIVELY MONITORING A PHYSIOLOGICAL CONDITION AND FOR INTERACTIVELY PROVIDING HEALTH RELATED INFORMATION

FIELD OF THE INVENTION

This invention relates to the field of health monitoring devices. More specifically, the invention relates to educational and interactive health monitoring devices.

BACKGROUND OF THE INVENTION

Virtually everyone in the modern world is touched by the high cost of health care. With rising costs, fewer and fewer people can afford an optimal level of contact with a physician for treatment of health conditions or preventative care. This situation may lead many members of the population who are in need of health care to believe they cannot afford it. These persons are less likely to seek proper health care when needed.

Further, despite great advances in the field of medicine, there may still be some members of the population who feel threatened by or who harbor a distrust or fear of health care professionals or institutions, for any number of reasons. These persons are also less likely to seek proper health care when needed.

The two factors mentioned above: the high cost of health care and distrust or fear of health care professionals or institutions, may combine in members of the population to prevent such persons from seeking out and obtaining adequate health care.

Therefore, what is needed is a device which can reduce health care costs by performing some functions of a health care professional and at the same time reduce possible distrust of health care professionals and institutions by providing health care functions to a user in a non-threatening manner.

It is an object of the present invention to reduce health care costs by performing some functions of a health care professional.

It is yet a further object of the present invention to achieve the above-mentioned objects through education obtained in an enjoyable and interactive manner.

It is an additional object of the present invention to accomplish the above-mentioned objects in a relatively inexpensive and simple-to-use manner.

It is yet an additional object of the present invention to have the capability to be functionally expanded with interchangeable compact disks further reducing initial cost.

The prior art discloses devices that monitor health related parameters. For example, U.S. Pat. No. 5,307,263 discloses a modular, microprocessor-based, health monitoring system. The hand-held unit has a display screen, a control button pad, interchangeable program cartridges and sensors for monitoring a variety of health care data. The program cartridges may include motivational and educational material related to use of the device, including step-by-step instructions. Acquired data may be transmitted to a data management unit via an interface cable and to a clearinghouse via telephone lines. A program cartridge for monitoring glucose levels and a glucose sensor is disclosed having the purpose of caring for children with diabetes. However, this device has the disadvantage of having a relatively small liquid crystal display screen, a limited ability to process and store data due to its small size, and limited on-time due to its battery power. Because this invention is directed to chronic ailments, its educational capabilities are likely limited to teaching how to use the device and to teaching about those chronic ailments to which it is directed.

Another example is disclosed in U.S. Pat. No. 4,803,625 which discloses a personal health monitor that measures a patient's weight, temperature, blood pressure and ECG waveform. A plurality of monitors may be coupled to a central computer via telephone lines. The central computer may prompt the patients to take medication, measure certain health parameters, supply answers to selected questions or determine patient symptoms based on patient responses to questions. The monitor transmits patient data to the central computer. The central computer compares collected patient data to expected values and triggers an alarm if the data falls outside a predetermined range. A disadvantage of this invention is that communication with a central computer is required in order to implement its educational capabilities. This increases the cost and complexity of the entire system.

Yet another example can be found in U.S. Pat. No. 5,024,225 which discloses a personal health monitor and its enclosure. The object of this invention is to provide an enclosure for a health monitor such as the one described in U.S. Pat. No. 4,803,625, discussed above. A disadvantage of this device is that it requires the use of a standard lap top computer as the processing unit which increases the cost of the device.

None of the above-mentioned patented devices benefit from the enhanced sound, video and memory capabilities of a multimedia processor having a CD-ROM digital memory store and operating with a television set.

SUMMARY OF THE INVENTION

The present invention is an electronic health monitoring system. A multimedia processor is a modified CD-ROM multimedia interactive television video game console which comprises a microprocessor, hardware, and software. One or more physiological data monitors are coupled to provide a signal representative of a user's physiological parameter, such as blood pressure, to the multimedia processor through an isolated interface circuit. A hand-held program controller having directional buttons is operated by the user to control the various functions of the multimedia processor. A television is coupled to the multimedia processor to provide sound and a video display based upon output signals from the multimedia processor. A monitor can also be used to provide a display platform.

Interchangeable compact disks (CD-ROM) comprise additional software. The software contained in the interchangeable compact disks enables the system to execute a variety of health related functions, to display high quality moving or still video images and to produce high quality sound accompaniment. For example, the system may monitor a user's electrocardiographic signals and display an ECG waveform and various other parameters, such as heart rate, on the television screen. The system may also interactively provide more detailed or educational information to the user based upon the user's operation of the hand-held program controller and also based upon predetermined software routines and data stored within the system.

DETAILED DESCRIPTION OF THE PREFERRED EMBODIMENT

Figure 1:
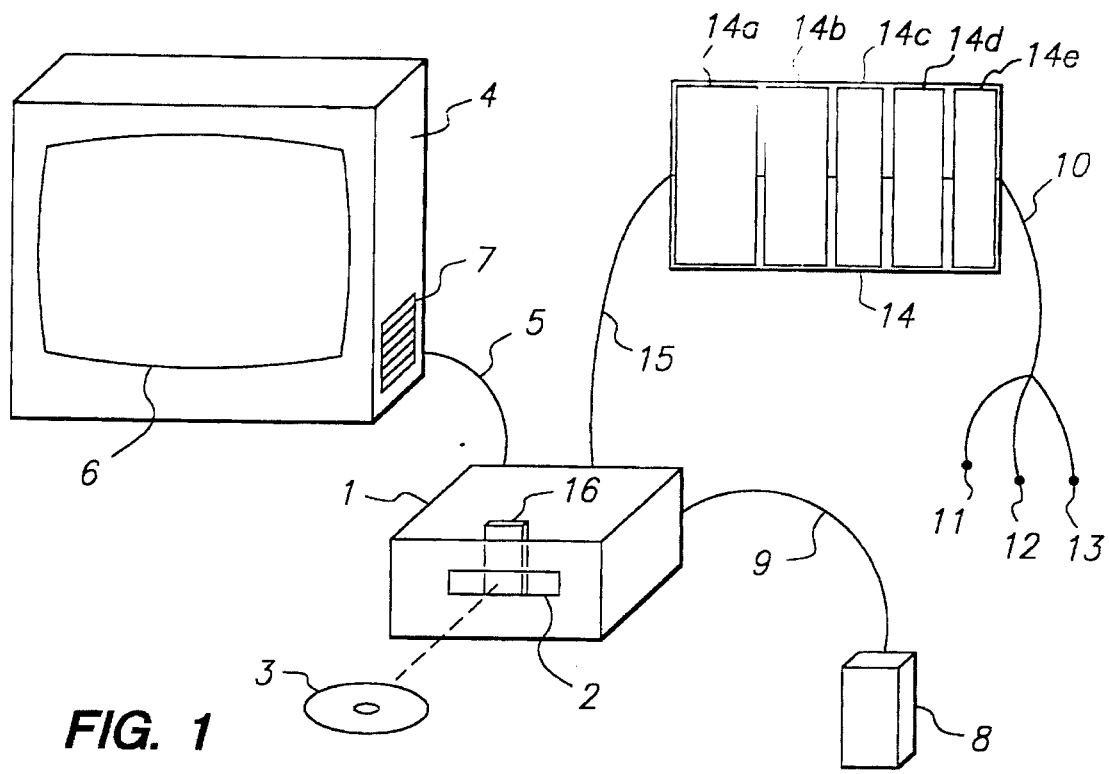
FIG. 1 shows a diagram of the present invention.
Figure 2:
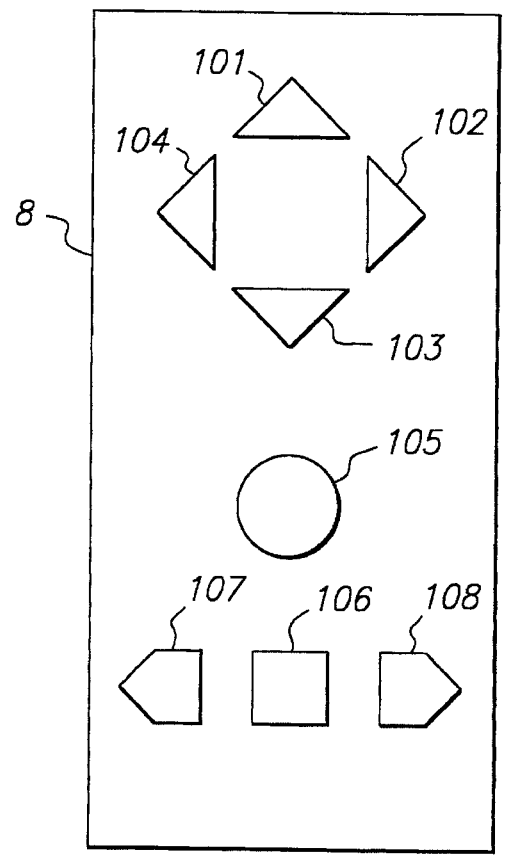
FIG. 2 shows a detailed diagram of the hand-held program controller of the present invention.

Referring to FIG. 1, a diagram of the present invention is shown. A multimedia processor 1 comprises a microprocessor, hardware, read-only digital memory (ROM), writeable digital memory (RAM), and may also include a compact disk read only memory (CD-ROM) drive for accepting interchangeable compact disks for an increased memory store. Data and software that is medically or health related and software routines for controlling the system are stored in one or more of the digital memory stores. In the preferred embodiment, the multimedia processor 1 is a CD-ROM television video game console, otherwise known as an "interactive TV" (ITV) system such as the Interactive Multiplayer developed by 3DO Company and manufactured by Panasonic under the name "FZ-1 REAL 3DO Interactive Multiplayer" or another similar ITV system manufactured under license from 3DO. The multimedia processor 1 is somewhat smaller in size than a typical video cassette recorder (VCR). Alternately, the multimedia player 1 is a "set-top box" which is television compatible, has interactive capabilities and has one or more communication ports which may connect to the "information superhighway" through a telephone line, coaxial cable, or other means. Such a set-top box preferably includes an application specific integrated circuit (ASIC), programmed arithmetic logic array chip (PAL) or other circuit devices to implement functions of an interface device 14 described below. Preferably, the multimedia processor 1 also comprises a 32-bit reduced instruction set (RISC) central processing unit (CPU) made by ARM, a digital signal processor (DSP) for high quality sound, and has three dimensional audio imaging for increased directional realism in the sound effects. The multimedia processor 1 preferably has expansion ports to support additional user interface and other devices, such as keyboards, joysticks, trackballs, or modems in daisy chain fashion and to accept add-on circuits for enhanced sound, video, or processing performance. In addition, the multimedia processor 1 preferably comprises an "animation engine" having two integrated circuit chips for displaying or moving up 64 million pixels per second and having the ability to make a video image bend, twist, skew, shrink, stretch, be transparent or translucent, and having the ability to create light and shadow effects and having the ability to "wrap" a first two-dimensional video image onto a second three-dimensional video image of an object. Such video techniques are known in the art. The multimedia processor 1 has a slot 2 for accepting interchangeable compact disks 3 into the CD-ROM drive. The interchangeable compact disks 3 comprise additional software which enables the system to execute a variety of specific health related functions and interactions related to ECG, blood pressure, glucose levels, pulse rate, kidney functions and so forth. Alternatively, the interchangeable compact disks 3 are instead interchangeable cartridges, similar to interchangeable video game cartridges, having high density digital mass storage, such as flash memory cards. The multimedia processor 1 is coupled by a television interface cable 5 to a television 4 of the conventional type or to a television having enhanced video or sound capabilities. The multimedia processor 1 supplies electronic information to the television 4 through the television interface cable 5 to enable the television 4 to produce appropriate images on the television screen 6 and to enable the television 4 to project appropriate audio sounds from the television speaker 7 or speakers. Stereo sound effects may be employed in those televisions having stereo capability. In addition, auxiliary speakers or sound amplification devices may be coupled to the television 4. The multimedia processor 1 is also coupled to a program controller 8 by a control interface cable 9. The program controller 8 enables the user to make selections and to control the functions of the health monitoring system. The program controller 8 is also shown in FIG. 2 and is described in more detail below.

The multimedia processor 1 is also coupled to a physiological data monitor 10. The physiological data monitor 10 is coupled to the user's body to obtain electrical signals representative of a physiological parameter. The physiological data monitor 10 is coupled to the multimedia processor through an interface device 14. The interface device 14 includes hardware and software necessary to receive signals from the physiological data monitor 10 by means of the signal receiver 14(d), to perform signal conditioning or processing by means of the processor 14(b) and the convertor 14(c), to control the multimedia processor 1 by means of the multimedia controller 14(a), and to provide signals representative of a physiological parameter to the multimedia processor 1 through an interface cable 15. Such signal processing may include digital to analog conversion, analog to digital conversion, digital reformatting, and signal scaling and may be based upon the system hardware, software, user input or upon requirements of the physiological data monitor 10. Preferably, the physiological data monitor 10 is electrically isolated from the rest of the system by a patient isolating circuit 14(e). For example, such a patient isolating circuit may comprise an optically isolating circuit such as the "MAX250/MAX251" +5 volt powered isolated RS-232 driver/receiver manufactured by MAXIM. Preferably, the interface device 14 comprises the patient isolating circuit described above by being integrally housed within the same housing, however, the patient isolating circuit may be separately housed or incorporated into the physiological data monitor 10. In addition, the multimedia processor 1 may provide control signals to the interface device 14 through the interface cable 15 based upon the hardware and software in the multimedia processor 1 and upon the user's input to the program controller 8. Additionally, the program controller 8 may be coupled to provide control signals directly to the interface device 14. The interface device 14 may be external to the multimedia processor 1, but in the preferred embodiment, the interface device 14 and the interface cable 15 are integrally mounted internal to the housing of the multimedia processor 1 as is the patient isolating circuit.

As an example only, FIG. 1 shows a physiological data monitor 10 in the form of an electrocardiogram (ECG) monitoring device. The ECG monitoring device has three electrodes 11,12,13 which couple to the user's body to obtain analog electrical signals representative of the user's cardiac activity. However, the physiological data monitor 10 may comprise a pressure cuff, a temperature probe, a blood glucose sensor, kidney dialysis equipment, and so forth. Standard or modified patient monitoring equipment provided by other manufacturers may be used. For example, Johnson & Johnson makes a blood pressure cuff called "Dynamap" and Boehringer Mannheim makes a blood glucose indicator called "Accucheck Easy." Such patient monitoring equipment provided by other manufacturers often have an RS-232 port or analog output jacks. Therefore, to save manufacturing costs, the present invention includes the ability to interface with such types of connectors by including compatible connectors and related hardware in the interface device 14. Each of the various physiological data monitors 10 are interchangeable and each may have corresponding software stored on an interchangeable compact disk 3.

In an embodiment of the present invention, the multimedia processor 1 has selectable modes wherein a language such as English, French, German, Italian, or Spanish is selected and a level of sophistication or educational background of the user is selected. This may be implemented by a hardware switch coupled to the multimedia processor 1 or by a hidden software function which is accessible, for example, only when a specific combination of control buttons are activated during system power up. Such hidden software functions are known in the art. As an example of the use of the selectable modes, a doctor could select an appropriate language and level of sophistication of a user or patient using the hidden software function. The user then takes the system to the user's home and goes through an interactive health monitoring or an interactive educational program which is tailored to the language and level of sophistication or educational background of the user. The user then returns to the doctor's office with the system where information obtained from the patient is downloaded from the health monitoring system to a computer at the doctor's office. This information then enables the doctor to quickly pinpoint any problem areas that the particular patient is experiencing which saves the doctor's time, effecting a savings in medical resources. Then the system may be reconfigured for a different user having a different native language and level of sophistication or educational background and the process repeated.

Referring to FIG. 2, a hand-held program controller 8 is shown. The program controller 8 comprises a variety of push button switches. The push button switches are coupled to be activated by control buttons 101, 102, 103, 104, 105, 106, 107, 108, 109, and 110 which are manipulated by the user for controlling the health monitoring system. The program controller 8 has a group of directional control buttons 101,102,103 and 104 in the center of which is printed the label "SELECT." The button 105 is printed with the label "INDEX." The button 106 is printed with the label "HELP." The button 107 is printed with the label "GO." The button 108 is printed with the label "PAUSE." The button 109 has the label "BACK" printed on or near it. The button 110 has the label "FORWARD" printed on or near it. The specific configuration of the buttons and labels is by way of example only and it should be apparent that any number of alternate configurations of buttons, keys, or different labels would suffice to achieve the objects of the program controller 8.

As an example of how the health monitoring system operates, a user first sets up the system in a manner similar to setting up a television-type video game, such as that manufactured by 3DO. Next, an interchangeable compact disk 3 is inserted into the slot 2 of the multimedia processor 1. In this case, an ECG disk is installed. Then, the user connects the physiological data monitor 10 to the user's body. In this case, the ECG electrodes 11,12,13 are attached to the user's chest. Next, the user turns the system on. Then the software of the interchangeable compact disk 3 and the software of the multimedia processor 1 guide the user through a series of educational and interactive steps including measurements of physiological parameters and display of the results. In this case, for example, the health monitoring system may display on the television screen a moving or still image or images and possibly audio signals to explain what an ECG is, why ECG measurements are important to health care and to guide the user through the steps necessary to take ECG measurements. Then, the health monitoring system displays the results of the measurements and may have audio effects as well. In this case, the user's ECG trace or waveform may be displayed in analog form along with the user's heart rate in numerical form, while a audio representation of the user's beating heart may be present. The health monitoring system may also compare the user's measurements with previously stored measurements of the same user's ECG or with measurements representative of a normative physiological parameter. Based upon these comparisons, the system may guide the user through additional measurements, store information for later retrieval or downloading, recommend that the user seek the services of a health care professional, ask questions of the user, give advice in areas such as the user's diet and exercise habits, and so forth. In addition to the above, the health monitoring system may provide functions related to blood pressure, glucose levels, pulse rate, kidney function, and so forth.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention. Specifically, it will be apparent that to one of ordinary skill in the art that the device of the present invention could be implemented in several different ways and the apparatus disclosed above is only illustrative of the preferred embodiment of the invention and is in no way a limitation.

What is claimed is:

1. An apparatus for interactively monitoring a physiological condition and for interactively providing health-related information comprising:
  a. a television set;
  b. a multimedia processor coupled to provide audio and visual signals to the television set;
  c. an interface device coupled to control the multimedia processor;
  d. a physiological data monitor coupled to provide a signal representative of a physiological parameter of a user to the interface device;
  e. a patient isolating circuit coupled between the physiological data monitor and the interface device; and
  f. a program controller coupled provide a control signal to the multimedia processor based upon the user's input, so as to provide health related information to the user in an interactive manner based upon the signal representative of the physiological parameter and the control signal.

2. The apparatus according to claim 1 wherein the multimedia processor comprises a CD-ROM drive for accepting an interchangeable compact disk.

3. The apparatus according to claim 2 wherein the interchangeable compact disk stores health related educational material.

4. The apparatus according to claim 2 wherein the interchangeable compact disk comprises software for providing additional functionality to the apparatus.

5. The apparatus according to claim 1 wherein the interface device comprises;
  a. means for receiving the signal representative of a physiological parameter;
  b. means for converting the signal representative of a physiological parameter into a form acceptable to the multimedia processor coupled to the means for receiving; and
  c. means for controlling the multimedia processor coupled to the means for converting.

6. The apparatus according to claim 1 wherein the isolating circuit utilizes optical isolation.

7. The apparatus according to claim 1 wherein the isolating circuit is integral to the multimedia processor.

8. The apparatus according to claim 1 wherein the multimedia processor comprises a video game console.

9. The apparatus according to claim 8 wherein the video game console is a 3DO Interactive Multiplayer.

10. The apparatus according to claim 1 wherein the interface device is integral to the multimedia processor.

11. An apparatus for interactively monitoring a physiological condition and for interactively providing health-related information comprising:

a. a display device comprising a display screen and an audio speaker;

b. a multimedia processor coupled to provide an audio signal and a visual signal to the display device wherein the multimedia processor comprises a multiplayer having a CD-Rom drive;

c. an interface device coupled to control the multimedia processor;

d. a physiological data monitor coupled to provide a signal representative of a physiological parameter of a user to the interface device;

e. a patient isolating circuit coupled between the physiological data monitor and the interface device; and f. a program controller coupled provide a control signal to the multimedia processor based upon the user's input, so as to provide health related information to the user in an interactive manner based upon the signal representative of the physiological parameter and the control signal.

12. The apparatus according to claim 11 wherein the multimedia processor comprises a video game console.

13. The apparatus according to claim 12 wherein the video game console is a 3DO Interactive Multiplayer.

14. The apparatus according to claim 11 wherein the display device comprises a television set.

15. The apparatus according to claim 11 further comprising an interchangeable compact disk removably coupled to the CD-ROM drive for providing additional functionality to the apparatus.

16. The apparatus according to claim 11 further comprising an interchangeable compact disk removably coupled to the CD-ROM drive for storing health related educational material.

17. The apparatus according to claim 11 wherein the interface device comprises;

a. means for receiving the signal representative of a physiological parameter;

b. means for converting the signal representative of a physiological parameter into a form acceptable to the multimedia processor coupled to the means for receiving; and c. means for controlling the multimedia processor coupled to the means for converting.

18. The apparatus according to claim 11 wherein health related educational material is stored on a CD-ROM.

19. The apparatus according to claim 11 wherein the isolating circuit utilizes optical isolation.

20. The apparatus according to claim 11 wherein the isolating circuit is integral to the multimedia processor.

21. The apparatus according to claim 11 wherein the interface device is integral to the multimedia processor.

22. A method of interactively monitoring a physiological condition and for interactively providing health-related information comprising the steps of;

a. providing educational information related to a physiological parameter to a user by a multimedia processor, wherein the educational information is stored on a CD-ROM;

b. sensing an analog signal representative of a physiological parameter of the user wherein the analog signal is sensed by a physiological data monitor coupled to a patient isolating circuit of an interface device;

c. converting the analog signal into a stream of digital values to the multimedia processor, wherein the analog signal is converted by the interface device;

d. displaying physiological information derived from the digital values on a television screen.

23. An apparatus for interactively monitoring a physiological condition and for interactively providing health-related information comprising:

a. a physiological data monitor that is adapted to measure a physiological condition of a user and for generating a first electronic signal in response to a measurement of the physiological condition;

b. a processor for receiving a second electronic signal that is a function of the first electronic signal;

c. an interface isolating device coupled between the physiological data monitor and the processor for receiving the first electronic signal from the physiological data monitor and providing the second electronic signal to the processor, wherein the interface isolating device electrically isolates the user from the processor;

d. a memory coupled to the processor for storing a plurality of display information file, each file corresponding to a predetermined measurement of the physiological condition; and e. a display system coupled to the processor for displaying one of the display information files in response to the measurement of the physiological condition, so as to provide health related information to the user in an interactive manner.

24. The apparatus according to claim 23 wherein the processor comprises a CD-ROM drive for accepting an interchangeable compact disk.

25. The apparatus according to claim 24 wherein the interchangeable compact disk stores the display information files.

26. The apparatus according to claim 24 wherein the interchangeable compact disk comprises software for providing additional functionality to the apparatus.

27. The apparatus according to claim 23 wherein the interface isolating device utilizes optical isolation.

28. The apparatus for monitoring a physiological condition of a user according to claim 23 wherein the memory comprises an interchangeable compact disk.

29. The apparatus according to claim 23 wherein the display information files comprise the health related information.

30. The apparatus according to claim 23 wherein the display system is a television set.

* * * * *

(12) EX PARTE REEXAMINATION CERTIFICATE (7182nd)

United States Patent
Quy

(10) Number: US 5,601,435 C1
(45) Certificate Issued: Nov. 24, 2009

(54) METHOD AND APPARATUS FOR INTERACTIVELY MONITORING A PHYSIOLOGICAL CONDITION AND FOR INTERACTIVELY PROVIDING HEALTH RELATED INFORMATION

(75) Inventor: Roger J. Quy, Belvedere, CA (US)

(73) Assignee: Raya Systems, Inc., Mountain View, CA (US)

Reexamination Request:
No. 90/009,237, Aug. 1, 2008

Reexamination Certificate for:
Patent No.: 5,601,435
Issued: Feb. 11, 1997
Appl. No.: 08/334,643
Filed: Nov. 4, 1994

(51) Int. Cl.
*G09B 5/00* (2006.01)

(52) U.S. Cl. ............ 434/307 R; 434/262; 434/365; 345/501

(58) Field of Classification Search ............ None
See application file for complete search history.

(56) References Cited

U.S. PATENT DOCUMENTS

| | | |
|---|---|---|
| 3,808,502 A | 4/1974 | Babilius |
| 4,110,918 A | 9/1978 | James et al. |
| 4,749,354 A | 6/1988 | Kerman |
| 4,858,617 A | 8/1989 | Sanders |
| 5,226,431 A | 7/1993 | Bible et al. |
| 5,277,197 A | 1/1994 | Church et al. |
| 5,307,263 A | 4/1994 | Brown |
| 5,377,258 A | 12/1994 | Bro |

FOREIGN PATENT DOCUMENTS

WO        WO 93/02622        2/1993

*Primary Examiner*—Beverly M. Flanagan

(57) ABSTRACT

An electronic health monitoring system. A multimedia processor is a modified CD-ROM multimedia interactive television video game console which comprises a microprocessor, hardware, and software. One or more physiological data monitors are coupled to provide a signal representative of a user's physiological parameter to the multimedia processor through an isolated interface circuit. A hand-held program controller with directional buttons is operated by the user to control the various functions of the multimedia processor. A television is coupled to the multimedia processor to provide sound and a video display based upon output signals from the multimedia processor.

Interchangeable compact disks (CD-ROM) comprise additional software. The software contained in the interchangeable compact disks enables the system to execute a variety of health related functions, to display high quality moving or still video images and to produce high quality sound accompaniment. For example, the system may monitor a user's electrocardiographic signals and display an ECG waveform and various other parameters, such as heart rate, on the television screen. The system may also interactively provide more detailed or educational information to the user based upon the user's operation of the hand-held program controller and also based upon predetermined software routines and data stored within the system.

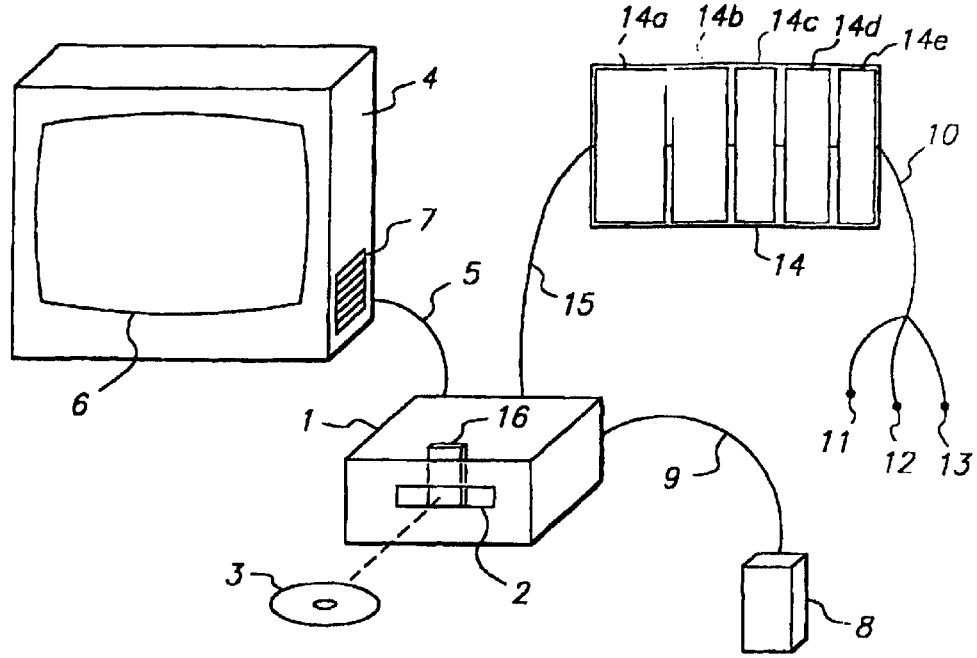

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 23, 25, 26 and 27–29 are determined to be patentable as amended.

Claims 24 and 30 dependent on an amended claim, are determined to be patentable.

New claims 31 and 32 are added and determined to be patentable.

Claims 1–22 were not reexamined.

23. An apparatus for interactively monitoring a physiological condition and for interactively providing health-related information comprising:
   a. a physiological data monitor that is adapted to measure [a] *the* physiological condition of a user and for generating a first electronic signal in response to a measurement of the physiological condition;
   b. a processor for (*i*) receiving a second electronic signal that is a function of the first electronic signal *and (ii) comparing the measurement with a plurality of normative values*;
   c. an interface isolating device coupled between the physiological data monitor and the processor for receiving the first electronic signal from the physiological data monitor and providing the second electronic signal to the processor, wherein the interface isolating device electrically isolates the user from the processor;
   d. a memory coupled to the processor for storing a plurality of display information [file], each [file] *of the plurality of display information* corresponding to a [predetermined measurement] *different one of the normative values* of the physiological condition; and
   e. a display system coupled to the processor for displaying one of the *plurality of* display information [files] in response to *the comparing of* the measurement of the physiological condition *with the normative values*, so as to provide *the* health related information to the user in an interactive manner.

25. The apparatus according to claim 24 wherein the interchangeable compact disk stores the *plurality of* display information [files].

26. The apparatus according to claim [24] *23* wherein the [interchangeable compact disk] *memory additionally* comprises [software] *a program of instructions* for providing additional functionality to the apparatus *such that the apparatus guides the user through one or more additional measurements in response to the comparing*.

27. The apparatus according to claim 23 wherein the interface isolating device utilizes optical isolation *within a single chip receiver/transmitter*.

28. The apparatus [for monitoring a physiological condition of a user] according to claim 23 wherein the memory *additionally* comprises [an interchangeable compact disk] *a program of instructions that recommends the user seek services of a health care professional based on the comparing*.

29. The apparatus according to claim 23 wherein the *plurality of* display information [files] comprise the health related information *for diet and exercise*.

*31. The apparatus according to claim 23, further comprising a controller separate from the display system, directly connected to the processor and configured to provide a plurality of control signals to the processor based upon a plurality of inputs received from the user, thereby to cause the health related information to be provided to the user based upon the second electronic signal and the control signals.*

*32. The apparatus according to claim 31, wherein at least one of the control signals is provided directly to the interface isolating device.*

\* \* \* \* \*